US011147537B2

(12) United States Patent
Duric et al.

(10) Patent No.: US 11,147,537 B2
(45) Date of Patent: Oct. 19, 2021

(54) METHOD FOR REPRESENTING TISSUE STIFFNESS

(71) Applicant: Delphinus Medical Technologies, Inc., Novi, MI (US)

(72) Inventors: Nebojsa Duric, Novi, MI (US); Peter Littrup, Novi, MI (US); Cuiping Li, Novi, MI (US); Olivier Roy, Novi, MI (US); Steven Schmidt, Novi, MI (US)

(73) Assignee: DELPHINUS MEDICAL TECHNOLOGIES, INC., Novi, MI (US)

( * ) Notice: Subject to any disclaimer, the term of this patent is extended or adjusted under 35 U.S.C. 154(b) by 390 days.

(21) Appl. No.: 16/182,715

(22) Filed: Nov. 7, 2018

(65) Prior Publication Data

US 2019/0117194 A1 Apr. 25, 2019

Related U.S. Application Data

(62) Division of application No. 14/703,746, filed on May 4, 2015, now Pat. No. 10,143,443.

(Continued)

(51) Int. Cl.
*A61B 8/00* (2006.01)
*A61B 5/00* (2006.01)
(Continued)

(52) U.S. Cl.
CPC .............. *A61B 8/485* (2013.01); *A61B 8/085* (2013.01); *A61B 8/0825* (2013.01); *A61B 8/15* (2013.01);
(Continued)

(58) Field of Classification Search
None
See application file for complete search history.

(56) References Cited

U.S. PATENT DOCUMENTS 3,154,067 A 10/1964 Stenstrom et al.
3,771,355 A 11/1973 Sachs
(Continued)

FOREIGN PATENT DOCUMENTS

AU 3443295 A 5/1996
EP 0284055 A2 9/1988
(Continued)

OTHER PUBLICATIONS

Andre et al., "A New Consideration of Diffraction Computed Tomography for Breast Imaging: Studies in Phantoms and Patients," Acoustical Imaging, 21, 379 (1995).
(Continued)

*Primary Examiner* — Patricia J Park
(74) *Attorney, Agent, or Firm* — Wilson Sonsini Goodrich & Rosati

(57) ABSTRACT

A method and system for analyzing stiffness in a volume of tissue, the method including: emitting acoustic waveforms toward the volume of tissue with an array of ultrasound transmitters; detecting, with an array of ultrasound receivers, a set of acoustic signals derived from acoustic waveforms transmitted through the volume of tissue; generating, from the set of acoustic signals, a sound speed map and an acoustic attenuation map of a region of the volume of tissue, generating a stiffness map derived from combination of a set of sound speed parameter values of the sound speed map and a corresponding set of acoustic attenuation parameter values of the acoustic attenuation map, the stiffness map representing the distribution of the stiffness parameter across the region; and at a display in communication with the computer processor, rendering a stiffness image of the volume of tissue, based upon the stiffness map.

20 Claims, 8 Drawing Sheets

Related U.S. Application Data

(60) Provisional application No. 61/988,308, filed on May 5, 2014, provisional application No. 62/047,523, filed on Sep. 8, 2014.

(51) Int. Cl.
*A61B 8/08* (2006.01)
*A61B 8/15* (2006.01)

(52) U.S. Cl.
CPC .............. *A61B 8/406* (2013.01); *A61B 8/461* (2013.01); *A61B 8/463* (2013.01); *A61B 8/5207* (2013.01); *A61B 8/5223* (2013.01)

(56) References Cited

U.S. PATENT DOCUMENTS

| | | |
|---|---|---|
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,363,326 A | 12/1982 | Kopel |
| 4,412,288 A | 10/1983 | Herman |
| 4,431,008 A | 2/1984 | Wanner et al. |
| 4,481,948 A | 11/1984 | Sole |
| 4,515,165 A | 5/1985 | Carroll |
| 4,542,744 A | 9/1985 | Barnes et al. |
| 4,564,019 A | 1/1986 | Miwa |
| 4,606,342 A | 8/1986 | Zamba et al. |
| 4,671,256 A | 6/1987 | Lemelson |
| 4,733,562 A | 3/1988 | Saugeon |
| 4,858,124 A | 8/1989 | Lizzi et al. |
| 4,917,096 A | 4/1990 | Englehart et al. |
| 5,025,792 A | 6/1991 | Hon et al. |
| 5,029,476 A | 7/1991 | Metala et al. |
| RE33,672 E | 8/1991 | Miwa |
| 5,103,129 A | 4/1992 | Slayton et al. |
| 5,143,069 A | 9/1992 | Kwon et al. |
| 5,158,071 A | 10/1992 | Umemura et al. |
| 5,158,536 A | 10/1992 | Sekins et al. |
| 5,179,455 A | 1/1993 | Garlick |
| 5,212,571 A | 5/1993 | Garlick et al. |
| 5,255,683 A | 10/1993 | Monaghan |
| 5,267,566 A | 12/1993 | Choucair et al. |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa, Jr. et al. |
| 5,304,173 A | 4/1994 | Kittrell et al. |
| 5,318,028 A | 6/1994 | Mitchell et al. |
| 5,329,817 A | 7/1994 | Garlick et al. |
| 5,349,954 A | 9/1994 | Tiemann et al. |
| 5,372,138 A | 12/1994 | Crowley et al. |
| 5,413,108 A | 5/1995 | Alfano |
| 5,415,164 A | 5/1995 | Faupel et al. |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,513,639 A | 5/1996 | Satomi et al. |
| 5,524,630 A | 6/1996 | Crowley |
| 5,558,092 A | 9/1996 | Unger et al. |
| 5,573,497 A | 11/1996 | Chapelon |
| 5,582,173 A | 12/1996 | Li |
| 5,590,653 A | 1/1997 | Aida et al. |
| 5,590,657 A | 1/1997 | Cain et al. |
| 5,596,992 A | 1/1997 | Haaland et al. |
| 5,606,971 A | 3/1997 | Sarvazyan |
| 5,620,479 A | 4/1997 | Diederich |
| 5,640,956 A | 6/1997 | Getzinger et al. |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,715,825 A | 2/1998 | Crowley |
| 5,743,863 A | 4/1998 | Chapelon |
| 5,762,066 A | 6/1998 | Law et al. |
| 5,766,129 A | 6/1998 | Mochizuki |
| 5,785,663 A | 7/1998 | Sarvazyan |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dodd et al. |
| 5,833,627 A | 11/1998 | Shmulewitz et al. |
| 5,833,633 A | 11/1998 | Sarvazyan |
| 5,836,882 A | 11/1998 | Frazin |
| 5,836,894 A | 11/1998 | Sarvazyan |
| 5,846,202 A | 12/1998 | Ramamurthy et al. |
| 5,851,182 A | 12/1998 | Sahadevan |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,014,473 A | 1/2000 | Hossack et al. |
| 6,109,270 A | 8/2000 | Mah et al. |
| 6,117,080 A | 9/2000 | Schwartz |
| 6,146,897 A | 11/2000 | Cohenford et al. |
| 6,165,734 A | 12/2000 | Garini et al. |
| 6,245,017 B1 | 6/2001 | Hashimoto et al. |
| 6,256,090 B1 | 7/2001 | Chen et al. |
| 6,351,660 B1 | 2/2002 | Burke et al. |
| 6,385,474 B1 | 5/2002 | Rather et al. |
| 6,428,477 B1 | 8/2002 | Mason |
| 6,451,013 B1 | 9/2002 | Bays et al. |
| 6,574,499 B1 | 6/2003 | Dines et al. |
| 6,612,988 B2 | 9/2003 | Maor et al. |
| 8,663,113 B2 | 3/2014 | Schmidt et al. |
| 10,143,443 B2 | 12/2018 | Duric et al. |
| 2001/0051774 A1 | 12/2001 | Littrup et al. |
| 2004/0122325 A1 | 6/2004 | Chambers et al. |
| 2004/0152986 A1 | 8/2004 | Fidel et al. |
| 2005/0165309 A1 | 7/2005 | Varghese et al. |
| 2005/0196025 A1 | 9/2005 | Schofield |
| 2006/0084859 A1 | 4/2006 | Johnson et al. |
| 2007/0015949 A1 | 1/2007 | Kaiser |
| 2007/0167823 A1 | 7/2007 | Lee et al. |
| 2007/0282200 A1 | 12/2007 | Johnson et al. |
| 2008/0058682 A1 | 3/2008 | Azhari et al. |
| 2008/0294043 A1* | 11/2008 | Johnson ............... A61B 8/4477 600/437 |
| 2009/0076379 A1 | 3/2009 | Hamill et al. |
| 2009/0129556 A1 | 5/2009 | Ahn et al. |
| 2011/0152685 A1 | 6/2011 | Misono |
| 2011/0201928 A1* | 8/2011 | Duric ................... A61B 8/0825 600/438 |
| 2011/0201932 A1* | 8/2011 | Duric ................... A61B 8/0833 600/443 |
| 2012/0283566 A1 | 11/2012 | Li |
| 2013/0267850 A1 | 10/2013 | Berman |
| 2014/0114189 A1 | 4/2014 | Kanayama et al. |
| 2014/0276068 A1 | 9/2014 | Szpak et al. |
| 2014/0316269 A1 | 10/2014 | Zhang et al. |

FOREIGN PATENT DOCUMENTS

| | | | |
|---|---|---|---|
| EP | 0317049 A2 | 5/1989 | |
| EP | 0320444 A1 | 6/1989 | |
| EP | 0351610 A2 | 1/1990 | |
| EP | 0538241 A2 | 4/1993 | |
| EP | 0609922 A2 | 8/1994 | |
| EP | 0614651 A1 | 9/1994 | |
| EP | 0642762 A2 | 3/1995 | |
| EP | 0661029 A1 | 7/1995 | |

(56) References Cited

FOREIGN PATENT DOCUMENTS

| | | |
|---|---|---|
| EP | 0774276 A2 | 5/1997 |
| WO | WO-9947046 A1 | 9/1999 |

OTHER PUBLICATIONS

Candy et al., "Signal Processing: The Model-Based Approach," (McGraw Hill. 1986), pp. 178-213.
Chan et al., An Agglomeration Multigrid Method for Unstructured Grids, Contemporary Mathematics, vol. 218, 1998.
Chang et al., Kirchhoff migration of ultrasonic images, Materials evaluation, V59, N3, 413-417, 2001.
Chelfouh et al., "Characterization of Urinary Calculi: in Vitro Study of 'Twin king Artifact' revealed by Color-Flow Sonography," AJR Am. J. Roentgenol., 171(4), (1998), 1055-60.
Greenleaf et al., "Introduction to Computer Ultrasound Tomography," Computer Aided Tomography and Ultrasonics in Medicine, (1979), North-Holland, 125-136.
Greenleaf et al., "Multidimensional Visualization of Ultrasonic Images," J Acoust Soc Amer, 95 (1994), 2902.
Greenleaf, "Tissue Characterization with Ultrasound: vol. II: Results and Applications," CRC Press, Inc., Boca Raton, Florida, pp. 95-122.
Harmuth, "Sequency Theory: Foundations and Applications, Advances in Electronics and Electron Physics," (Academic Press, 1977) 18-95.
Haykin, "Neural Networks—A Comprehensive Foundation," Prentice Hall, (1994), 236-284.
Hebden et al., "Acoustically Modulated Electrical Impedance Tomography, "Proc SPIE, 1231 (1990), 7-14.
Klimes, et al., Grid Travel-time Tracing: Second-order Method for the First Arrivals in Smooth Media, PAGEOPH, 1996, 148:539-63.
Li et al., Breast Imaging Using Transmission Ultrasound: Reconstructing Tissue Parameters of Sound Speed and Attenuation, 2008 International Conference on BioMedical Engineering and Informatics, IEEE Computer Society, 708-712.
Li et al., Comparison of Ultrasound Attenuation Tomography Methods for Breast Imaging, Medical Imaging 2008: Ultrasonic Imaging and Signal Processing, Proc. of SPIE., vol. 6920, 692015-(1-9), 2008.
Li et al., Refraction Corrected Transmission Ultrasound Computed Tomography for Application in Breast Imaging, Med. Phys. 37(5), May 2010, 2233-2246.
Louvar et al., "Correlation of Color Doppler Flow in the Prostate with Tissue Microvascularity," Cancer 1 :83(1), (1998), 135-40.
McCormick et al., Multigrid Solution of a Linearized, regularized least-squares problem in electrical impedance tomography, Inverse Problems 9, 1993, 697-713.
Mitchell, An Introduction to Genetic Algorithms, pp. 8-11. 35-78. 155-179 (MIT Press, 1996).
Nelson et al., "Interactive Acquisition, Analysis and Visualization of Sonographic Volume Data," International J Imaging Sys and Tech, 8(26), (1997), 26-37.
"Notice of Allowance dated Aug. 1, 2018 for U.S. Appl. No. 14/703,746.".
Oh et al., Multigrid Tomographic Inversion with Variable Resolution Data and Image Spaces, IEEE Transactions on Image Proessing, vol. 15, No. 9, Sep. 2006.
Quan et al., Sound-speed Tomography using First-arrival Transmission Ultrasound for a Ring Array, Medical Imaging 2007: Ultrasonic Imaging and Signal Processing, Proc. of SPIE, vol. 6513.
Schmidt et al., "Modification of Kirchhoff Migration with Variable Sound Speed and Attenuation for Tomographic Imaging of the Breast," Proc. of SPIE, vol. 7968, Mar. 25, 2011.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Scientific Assembly and Annual Meeting, Nov. 29-Dec. 4, 1998, presented in McCormick Place, Chicago, Illinois, vol. 209, listing: 1154 (1998).
U.S. Appl. No. 14/703,746 Office Action dated Feb. 13, 2018.
Walach et al., Local Tissue Attenuation Images Based on Pulsed-Echo Ultrasound Scans, IEEE Transactions on Biomedical Engineering, vol. 36. No. 2, Feb. 1989.
Zhang et al., a Comparison of Material Classification Techniques for Ultrasound Inverse Imaging, J. Acoust. Soc. Am., 111 (1), Pt. 1, Jan. 2002.

* cited by examiner

Table 1: Phantom Study Summary

| Mass ID # | Size (mm) | Mass Type | Clock Position | Stiffness Estimate | True Stiffness (from Manufacturer) |
|---|---|---|---|---|---|
| 1 | 12mm | Cancer | 7:00 | Stiff | Stiff |
| 2 | 12mm | Fibroadenoma | 10:00 | Stiff | Stiff |
| 3 | 12mm | Cyst | 2:00 | Soft | Soft |
| 4 | 8mm | Fibroadenoma | 12:00 | Stiff | Stiff |
| 5 | 8mm | Cyst | 4:00 | Soft | Soft |
| 6 | 8mm | Fibroadenoma | 10:00 | Stiff | Stiff |
| 7 | 8mm | Cyst | 2:00 | Soft | Soft |

FIGURE 7A

Table 4: In-Vivo Study Summary

| Study # | Breast Size | Breast Density | Lesion Pathology | Reported Lesion Position | Average Lesion Size (cm) | SoftVue stiffness assessment |
|---|---|---|---|---|---|---|
| SV021 | C | Dense | Cancer | 8:00 | 2.5 | Stiff |
| SV022 | DD | Scattered | Fibroadenoma | 1:30 | 3.0 | Stiff |
| SV045 | C | Scattered | Cancer | 10:00 | 1.8 | Stiff |
| SV077_1 | B | Extremely Dense | Cyst | 2:00 | 1.4 | Soft |
| SV077_2 | B | Extremely Dense | Cyst | 12:00 | 1.9 | Soft |
| SV077_3 | B | Extremely Dense | Cyst | 12:00 | 2.0 | Soft |
| SV079 | C | Heterogeneous | Cyst | 9:00 | 1.4 | Soft |
| SV089 | D | Scattered | Cancer | 9:30 | 1.7 | Stiff |
| SV090 | DDD | Heterogeneous | Fibroadenoma | 10:00 | 4.3 | Mixed |
| SV113 | DD | Scattered | Cyst | 2:00 | 1.8 | Mixed |
| SV114 | D | Scattered | Cancer | 10:00 RA | 1.2 | Stiff |
| SV117_1 | D | Dense | Fibroadenoma | 5:00 | 1.9 | Mixed |
| SV117_2 | D | Dense | Fibroadenoma | 8:00 | 2.6 | Soft |

FIGURE 7B

| Table 5: Comparison with Elastography | | | | | | |
|---|---|---|---|---|---|---|
| Comparison # | Breast Size | Breast Density | Lesion Pathology | SoftVue Stiffness Estimate | Toshiba Stiffness Estimate | Lesion Size (cm) |
| 1 | DD | Scattered | Cancer | Stiff | Stiff | 2.6 |
| 2 | B | Scattered | Fibroadenoma | Stiff | Stiff | 2.9 |
| 3 | DD | Scattered | Fibroadenoma | Mixed | Mixed | 1.6 |
| 4 | B | Extremely Dense | Cyst | Soft | Soft | 1.4 |
| 5 | B | Extremely Dense | Cyst | Soft | Soft | 1.9 |
| 7 | DDD | Heterogeneous | Fibroadenoma | Stiff | Stiff/Mixed | 4.3 |
| 8 | B | Scattered | Cancer | Stiff | Stiff | 1.4 |
| 9 | A/B | Heterogenous | Cancer | Stiff | Stiff | 2.3 |
| 10 | D | Scattered | Cancer | Stiff | Stiff | 1.2 |
| 11 | D | Dense | Fibroadenoma | Mixed | Mixed | 1.9 |

METHOD FOR REPRESENTING TISSUE STIFFNESS

CROSS-REFERENCE

This application is a divisional application of U.S. application Ser. No. 14/703,746, filed May 4, 2015, which claims the benefit of U.S. Provisional Application Ser. No. 61/988,308, filed on May 5, 2014, and U.S. Provisional Application Ser. No. 62/047,523, filed on Sep. 8, 2014, which are each incorporated herein in their entirety by this reference.

TECHNICAL FIELD

This invention relates generally to the medical imaging field, and more specifically to an improved method and system for representing tissue stiffness in the ultrasound medical imaging field.

BACKGROUND

Early detection of breast cancer and other types of cancer is typically an important factor in successful treatment. Ultrasound tomography is a promising imaging modality that has the potential to improve medical imaging of tissue for screening and diagnosis purposes compared to conventional imaging techniques. For instance, mammography is the current standard for breast screening, but involves ionizing radiation that precludes frequent imaging, and mammography has low sensitivity for detection of cancer in patients with dense breast tissue, which leads to a relatively high false negative rate. As another example, magnetic resonance imaging (MRI) is prohibitively expensive for routine use and also has limited accessibility.

A basic principle of conventional ultrasound involves emitting an acoustic wave or beam along a focused path from a source transmitter, and allowing the wave to scatter (e.g. in reflection, refraction, diffraction, transmission) from tissue or other boundaries in its path. The scattered wave returns to a surface of one or more receiving elements, which can be centered around and/or include the transmitter(s). The time of travel can be converted into a depth distance by multiplying the time by an assumed speed of sound in the media. The received signal is then output to a graphical display for user interpretation. Some systems (e.g., systems implementing elastography techniques) allow for measurement of tissue stiffness; however, current methods of ultrasonic imaging, including those with stiffness measurement capability, have drawbacks and limitations. For instance, methods of generating an image can produce significant artifacts (e.g., shadowing, aberration) and image quality that degrades with tissue depth, thus making analysis of such images difficult. Also, current ultrasound systems and methods are typically configured to accommodate a small imaging region, resulting in difficulties in imaging and characterizing entire organs, such as the breast. As an additional factor, measurement of tissue parameters and provision of analyses derived from such measurement are limited in current systems due to deficiencies in current ultrasound systems and methods for generating and processing signals. Furthermore, the performance of ultrasound scanning is dependent on the skills of the operator and image quality can vary from user to user.

Thus, there is a need in the ultrasound imaging field to create an improved method and system for representing tissue stiffness. This invention provides such an improved method and system.

BRIEF DESCRIPTION OF THE DRAWINGS

FIGS. 7A-7C depict results of a specific application of an embodiment of a method and system for representing tissue stiffness.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
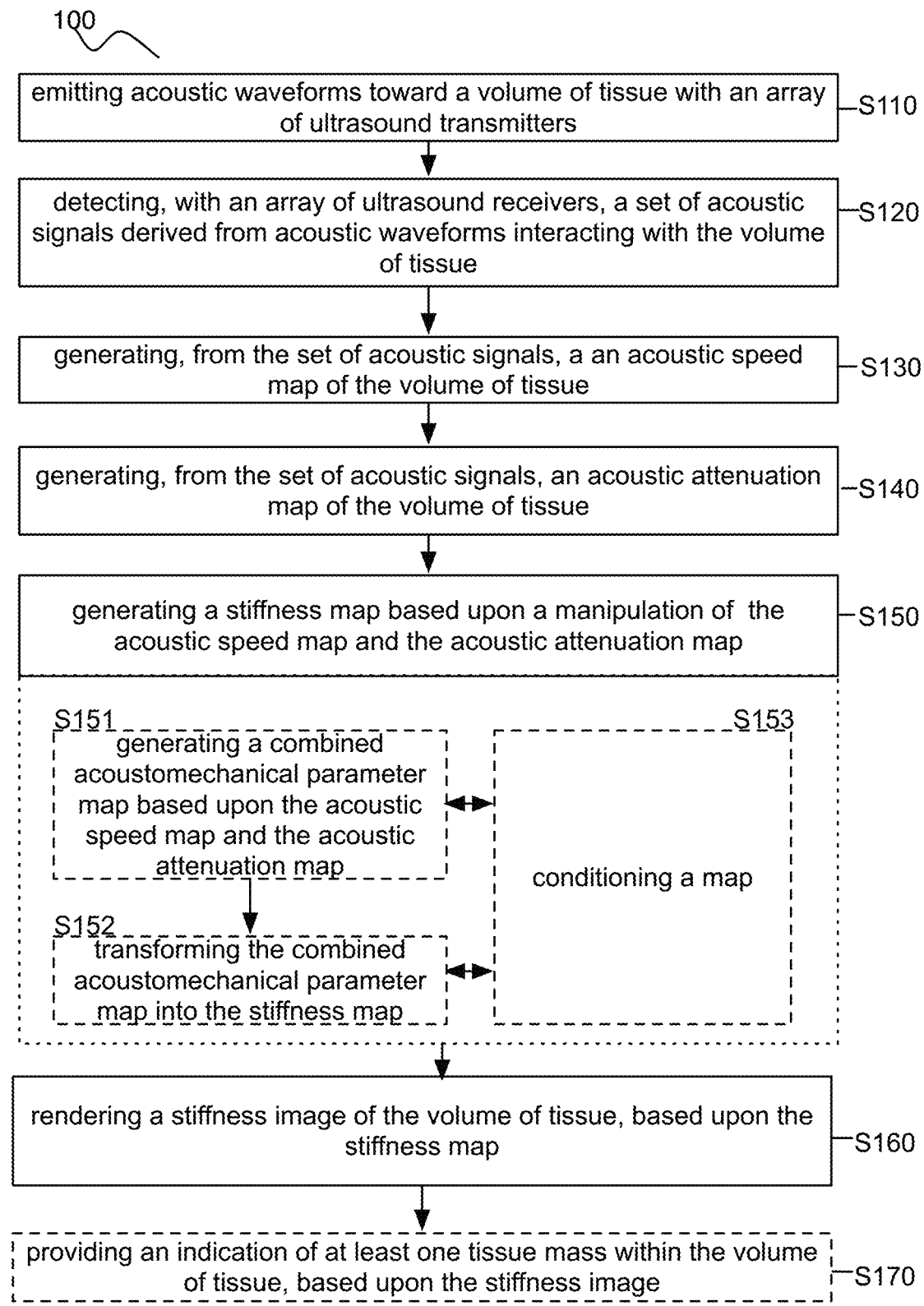
FIG. 1 is a schematic of a method for representing tissue stiffness.

In one embodiment, as shown in FIG. 1, a method 100 for analyzing a distribution of a stiffness parameter for a volume of tissue includes: emitting acoustic waveforms toward the volume of tissue with an array of ultrasound transmitters S110; detecting, with an array of ultrasound receivers, a set of acoustic signals S120 derived from acoustic waveforms interacting with the volume of tissue; generating, from the set of acoustic signals, a sound speed map of a region of the volume of tissue S130; generating, from the set of acoustic signals, an acoustic attenuation map of the region of the volume of tissue S140; generating a stiffness map based upon a manipulation of the sound speed map and the acoustic attenuation map S150; and rendering a stiffness image of the volume of tissue, based upon the stiffness map S160. In some variations, the method 100 can further include providing an indication of at least one tissue mass within the volume of tissue, based upon the stiffness image, at a user interface S170, which can provide information regarding presence of a cancerous mass, or risk of developing a cancerous mass within the volume of tissue.

The method 100 functions to render ultrasound images and/or generate transformed ultrasound data that can be used to provide an indication of a distribution of tissue stiffness within a volume of tissue (e.g., a whole breast, another organ). In some embodiments, the method 100 can function to produce images that are aligned with regulatory standards for medical imaging, as regulated, for instance, by the U.S. Food and Drug Administration (FDA). The method 100 is preferably used to characterize stiffness within tissue of a human breast, and more specifically, to characterize stiffness across the volume of a whole breast of a human patient. However, the method 100 can additionally or alternatively be used to characterize stiffness within tissue of an arm, leg, other appendage, and/or any suitable volume of tissue in a human or other animal. In relation to pathogenic masses, the method 100 can provide significant improvements over currently available methods and systems (e.g., mammographic methods and systems), in particular, for dense tissues. Even further, the method 100 can enable detection of node-negative invasive cancers that typically progress to a more severe stage prior to mammographic detection. In relation to current ultrasound methods and systems, the method 100 can improve sensitivity in detection of suspicious masses, while providing specificity in characterization of types of masses (e.g., in comparison to reflection ultrasound alone). The method 100 can, however, function to enable diagnosis, monitoring, and/or characterization of a volume of tissue in any other suitable manner.

In one embodiment, the method 100 is used to generate one or more renderings of regions of a volume of tissue that can be used to detect abnormalities (e.g., cancerous tissues) in a human or other animal. As such, in one variation the method 100 can be used to characterize stiffness within the tissue to facilitate detection of a mass present in a volume of tissue, categorize a mass (e.g., as a benign mass, as a malignant mass, as a cyst, as a cancerous mass, as a fibroadenoma, etc.) present in a volume of tissue, determine the severity or stage of a mass present in the volume of tissue (e.g., to determine whether a mass in the tissue is surgically removable), and/or to assess risk of cancer development (e.g., measuring breast tissue density) within the volume of tissue. In yet another embodiment, the method 100 can be used to characterize and/or investigate particular aspects of the tissue, such as to determine whether a mass in the tissue is a tumor, cyst, fibroadenoma, or other kind of mass. However, the method 100 can be used in any suitable application for imaging a volume of tissue or other suitable object. The method 100 is preferably implemented, at least in part, by way of an embodiment, variation, and/or example of the system 200 described in Section 2 below; however, the method 100 can additionally or alternatively be implemented using any other suitable system Block S110 recites: emitting acoustic waveforms toward the volume of tissue with an array of ultrasound transmitters, and Block S120 recites: detecting, with an array of ultrasound receivers, a set of acoustic signals derived from acoustic waveforms interacting with the volume of tissue. Blocks S110 and S120 function to gather acoustic data from which renderings of the volume of tissue can be derived in other Blocks of the method 100. Emitting acoustic waveforms preferably includes surrounding the volume of tissue with the array of ultrasound transmitters, and more preferably with a ring transducer comprising the array of ultrasound transmitters, wherein the ring transducer is configured to surround the volume of tissue with the array of ultrasound transmitters. The acoustic waveforms can be characterized by frequencies of approximately 1-20 MHz, or any suitable frequency for medical imaging or other applications. The detected acoustic signals of Block S120 are preferably derived from interactions between the emitted acoustic waveforms of Block S110 and the tissue, wherein interactions can include one or more of: scattering (e.g., reflection, refraction, diffraction, diffusion, etc.) and transmission of the acoustic waves through the tissue. The acoustic signals can travel along a straight, bent, zig-zag, or curved path, or a path of any suitable shape as determined by the physics of acoustic wave propagation.

Figure 2A:
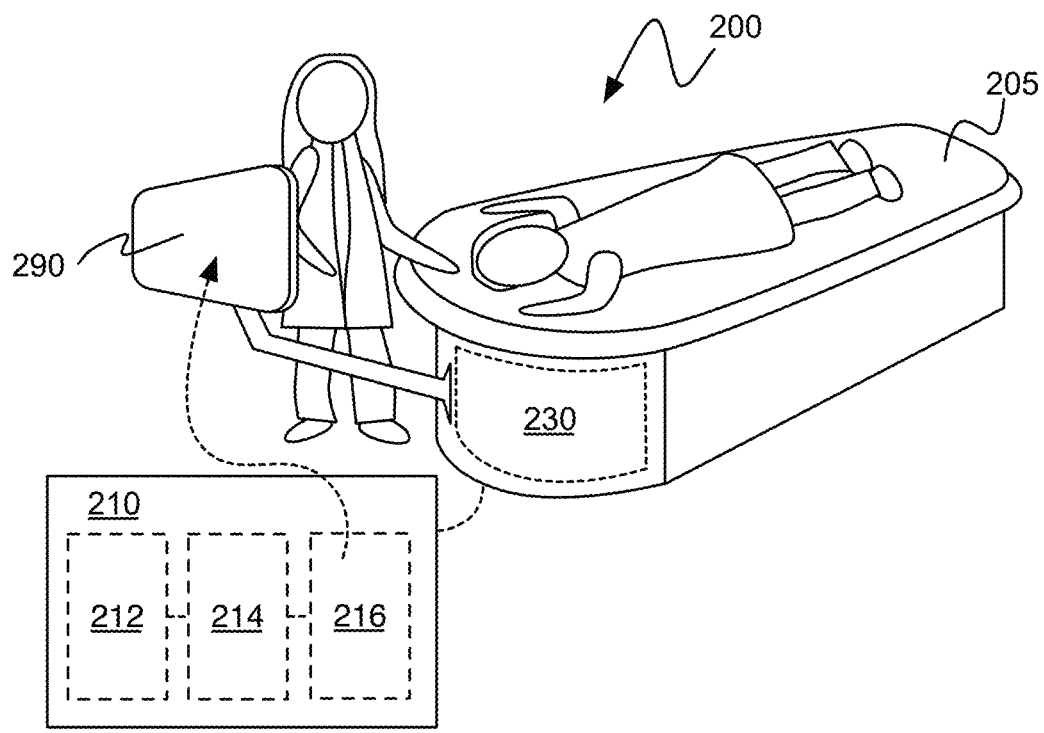
FIGS. 2A-2C are schematics of an embodiment of a system configured to implement at least a portion of a method for representing tissue stiffness.

In Blocks S110 and S120, emitting acoustic waveforms and detecting a set of acoustic signals can be performed with an ultrasound tomographic scanner 200 and methods similar to those described in U.S. Pat. Nos. 6,385,474 and 8,663,113, and U.S. Publication Nos. 2011/0201932 and 2013/0041261, which are each incorporated in its entirety by this reference. However, any suitable ultrasound device or scanner may be used. As shown in FIG. 2A, the steps of scanning the tissue and detecting acoustic signals are preferably performed during a scan of a patient lying prone on their stomach on a scanner table 205 having an opening that provides access to the volume of tissue of the patient. The table, which may be made of a durable, flexible material (e.g., flexible membrane, fabric, etc.), preferably contours to the patient's body, thereby increasing scanning access to the axilla regions of the breast and increasing patient comfort. The opening in the table allows the breast (or other appendage) to protrude through the table and be submerged in an imaging tank 230 filled with water or another suitable fluid as an acoustic coupling medium that propagates acoustic waves.

Figure 2B:
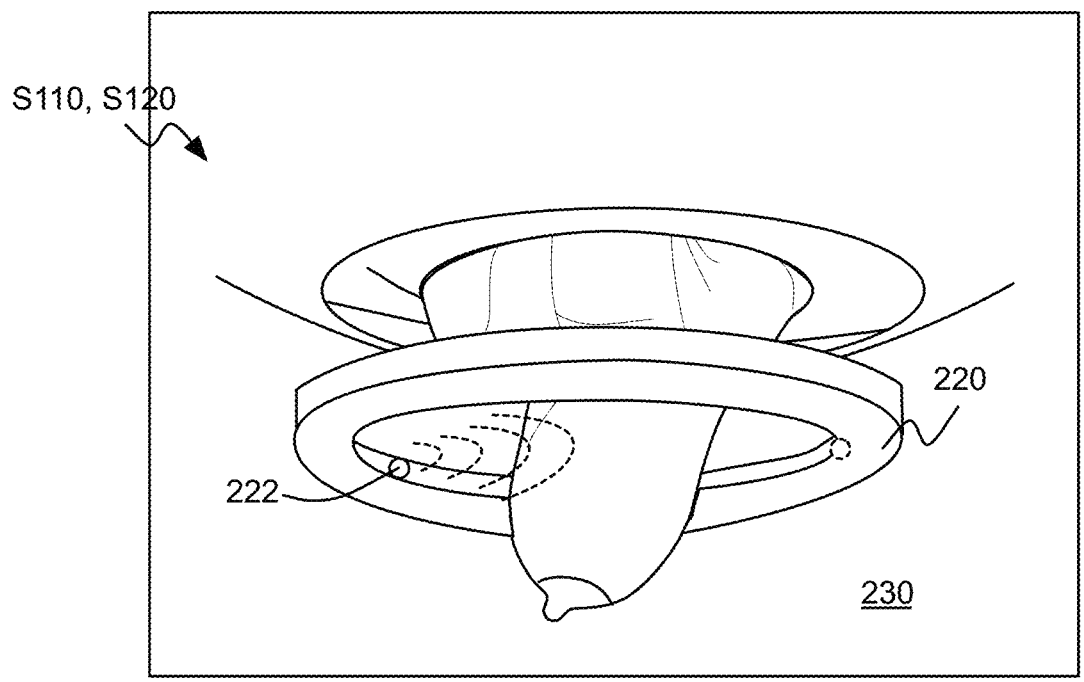
Figure 2C:
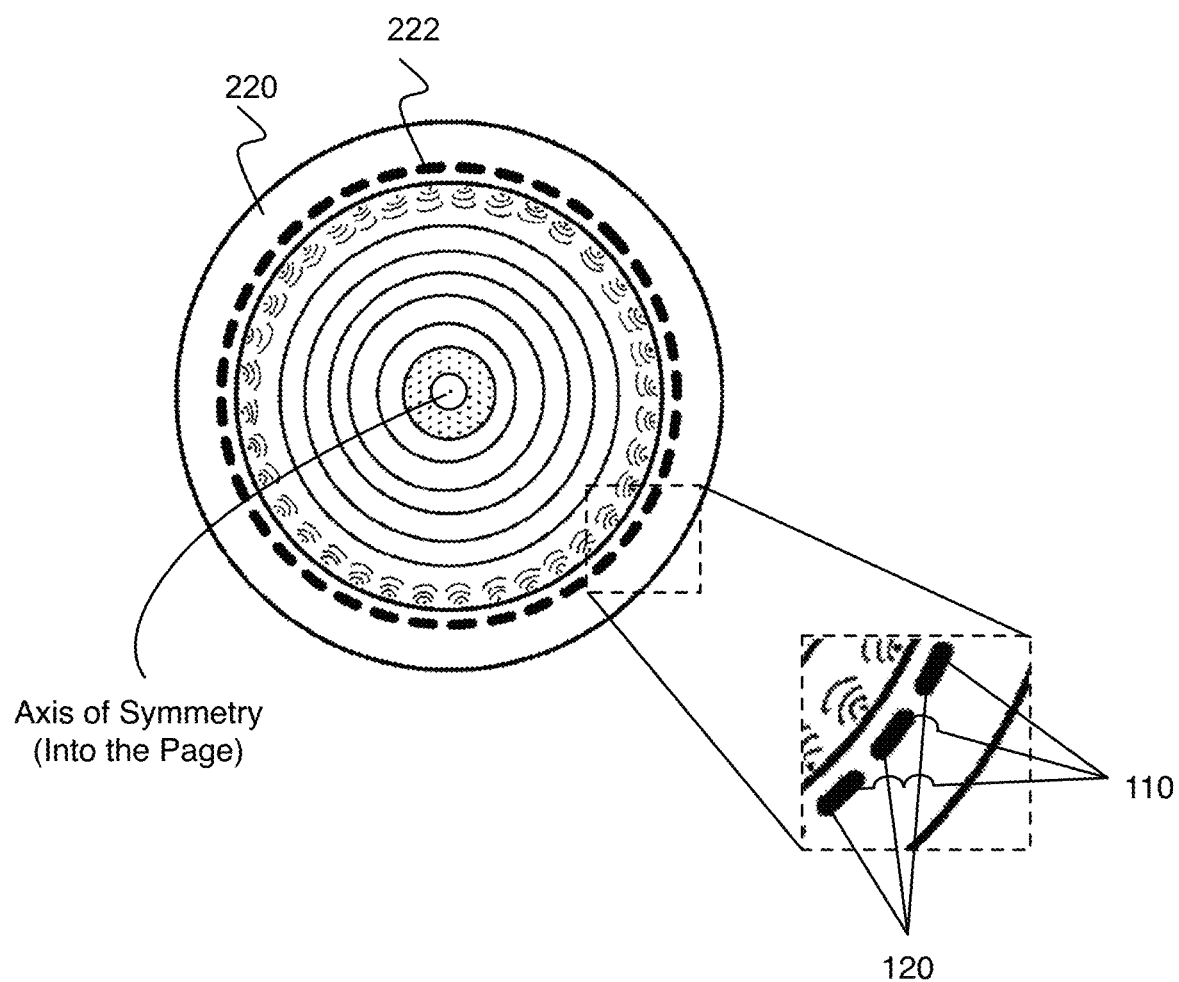

As shown in FIGS. 2B and 2C, a ring-shaped transducer 220 with transducer elements 222 can be located within the imaging tank and encircle or otherwise surround the breast, wherein the transducer elements 222 can comprise an array of ultrasound transmitters 110 and/or an array of ultrasound receivers 120. Multiple ultrasound transmitters 110 that direct safe, non-ionizing ultrasound pulses toward the tissue, and multiple ultrasound receivers 120 that receive and record acoustic signals scattering from the tissue and/or transmitted through the tissue, are distributed around the ring transducer 220, and in one configuration, can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 2C. During the scan, the ring transducer 220 moves to image all of the targeted tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The ring transducer 220 can be configured to scan step-wise in increments or travel continuously from the chest wall towards the nipple, and/or from the nipple towards the chest wall. However, the ring transducer 220 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014, which is hereby incorporated in its entirety by this reference. Furthermore, in a specific example, Blocks S110 and/or S120 can implement a ring transducer 220 having 2048 transducer elements in cooperation with an ultrasound tomographic scanner 200 having 512 receive channels, 512 transmit channels, an operating frequency of 3 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. However, Blocks S110 and/or S120 can additionally or alternatively be implemented using any other suitable patient interface system.

Emitting and detecting in Blocks S110 and S120 are preferably performed in a rapid manner, such as with a data acquisition time of less than approximately 1 second per "slice", which may help to avoid motion artifacts in the subsequent morphology renderings and enables the use of contrast agents. However, any other suitable acquisition time can characterize emitting acoustic waveforms and/or detecting acoustic signals as in Blocks S110 and S120. The emitted waveforms and/or detected signals can additionally or alternatively be beamformed on a transducing element. In some embodiments, however, Blocks S110 and/or S120 of the method 100 can, however, additionally and/or alternatively include retrieving acoustic signals from a storage device such as a hard drive or an online server. Furthermore, in relation to detecting acoustic signals, the method 100 can additionally or alternatively include processing the set of acoustic signals according to at least one conditioning algorithm. For instance, for a given transmitter/detector pair of transducers, processing the set of acoustic signals can include one or more of: reading and correcting the raw data (detected acoustic signals) for DC variation; implementing a trapezoidal filter to bandpass useful frequencies and cut noise; and implementing any other suitable filter (high pass, low pass, etc.) to filter desired frequencies. Further signal processing can additionally or alternatively include discarding unusable signal such as "muting" in which recorded signal before the transmission wavefront and/or and after the longest applicable receiving time (e.g. "top muting" or "bottom muting"), further noise reduction processes, and other suitable signal processing steps. However, any other suitable conditioning process can additionally or alternatively be used.

Block S130 recites: generating, from the set of acoustic signals, a sound speed map of a region of the volume of tissue, which functions to generate a sound speed map that can be used to generate a stiffness map that characterizes tissue stiffness, as in Block S150. Block S130 is preferably implemented at a processing system (e.g., a computer processor) included with or coupled to the ultrasound tomographic scanner 200 of Blocks S110 and S120, but can additionally or alternatively be implemented at any other suitable processing system. The sound speed map is preferably based upon processing of through-transmission signals of the set of acoustic signals, which are received in Blocks S110 and S120 in addition to backscattered signals from the volume of tissue. Preferably, generation of the sound speed map ($I_S$), includes generating a set of 2D slices representing sound speed, wherein each slices in the set of 2D slices represents a distribution of a sound speed parameter (e.g., a speed of sound at each of a set of regions within the volume of tissue) within the tissue, to form a stack of 2D slices for sound speed within the tissue. In a specific example, the stack of 2D slices corresponds to regions of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). Each sound speed slice preferably includes multiple elements (e.g., pixels in a grid) such that each element has an associated value of the sound speed parameter for a respective region of the scan region, including the volume of tissue and the acoustic coupling medium (such as the fluid of the tank in which the tissue is submerged). Furthermore, each sound speed slice is preferably a planar slice; however, the stack of slices for sound speed can be generated in any other suitable manner.

Figure 3:
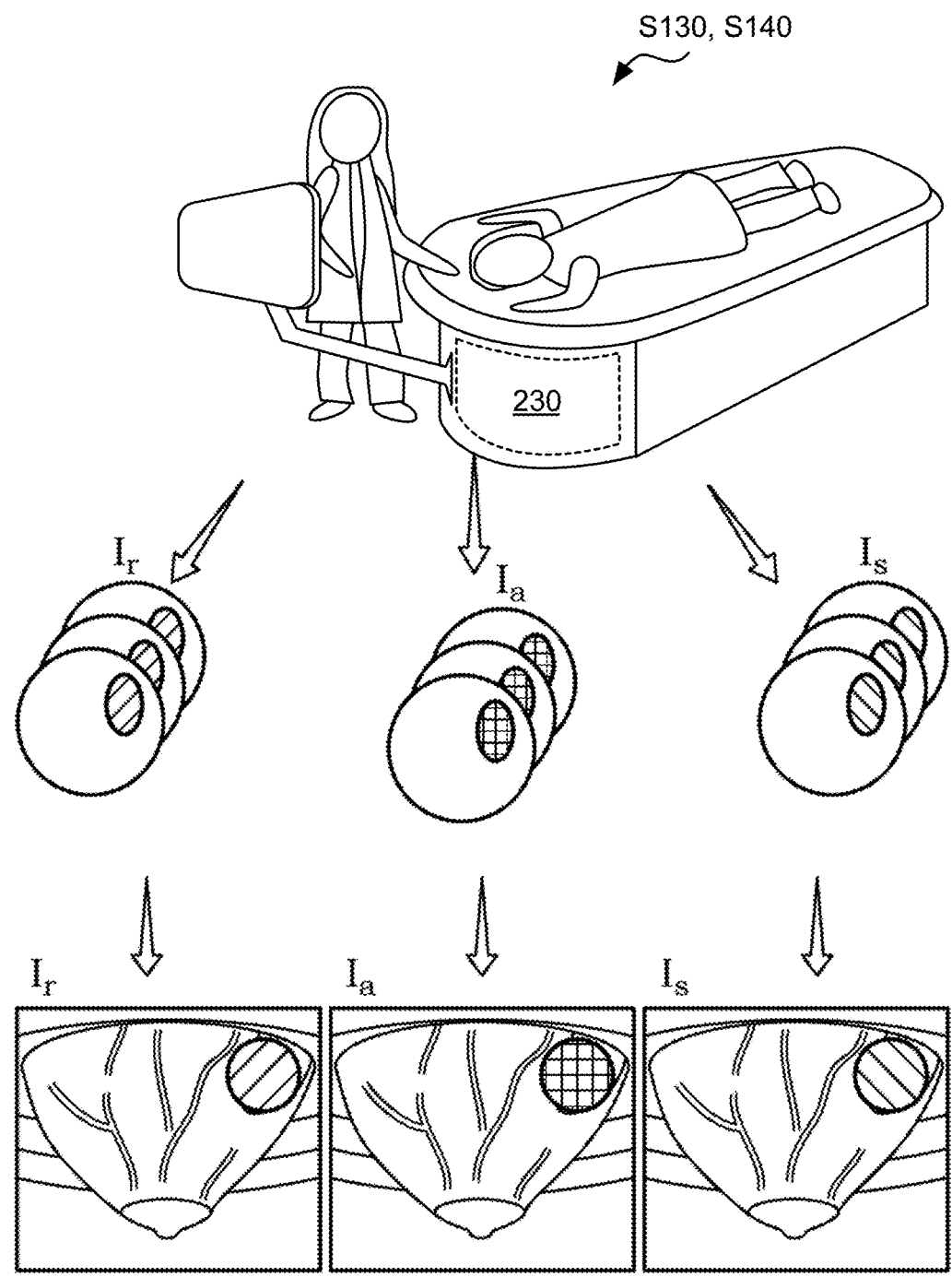
FIG. 3 depicts a portion of an embodiment of a method for representing tissue stiffness.

Generating a sound speed map in Block S130 can additionally or alternatively include generating a 3D sound speed map that is a volumetric representation of the sound speed parameter within the volume of tissue. In a first variation, as shown in FIG. 3, generating a 3D sound speed map can include combining a stack of 2D sound speed slices into a three-dimensional (3D) sound speed map. In a second variation, generating a 3D sound speed map can include transforming 3D volumetric acoustic data, obtained by scanning the tissue in a 3D manner, directly into a 3D sound speed map. Additionally or alternatively, the sound speed map can be generated using methods as described in U.S. Pat. No. 8,663,113 and/or U.S. Pub. No. 2012/0283566, filed on 23 Jul. 2012, which are each incorporated herein in its entirety by this reference.

Block S140 recites: generating, from the set of acoustic signals, an acoustic attenuation map of the region of the volume of tissue, which functions to generate an acoustic attenuation map that can be used to generate a stiffness map that characterizes tissue stiffness, as in Block S150. Similar to Block S130, Block S140 is preferably implemented at a processing system (e.g., a computer processor) included with or coupled to the ultrasound tomographic scanner 200 of Blocks S110 and S120, but can alternatively be implemented at any other suitable processing system. Similar to Block S130, and as shown in FIG. 3, generation of an acoustic attenuation map ($I_a$) can include generating a set of 2D slices representing acoustic attenuation, wherein each slice in the set of 2D slices represents a distribution of an acoustic attenuation parameter (e.g., a measure of energy loss of acoustic signal propagation for each of a set of regions within the volume of tissue) within the tissue, to form a stack of 2D slices for acoustic attenuation within the tissue. In a specific example, the stack of 2D slices corresponds to slices of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). The stack of 2D slices for acoustic attenuation generated in variations of Block S140 preferably correspond to (e.g., are associated with the same planes of) the stack of 2D slices for sound speed generated in variations of Block S130, in order to facilitate generation of the stiffness map in Block S150; however, the stack of 2D slices for acoustic attenuation can alternatively not correspond directly with the stack of 2D maps for sound speed (e.g., in variations wherein the sound speed map and the acoustic attenuation map are not generated from the same set of acoustic signals of Blocks S110 and S120). Each acoustic attenuation slice preferably includes multiple elements (e.g., pixels in a grid) such that each element represents a corresponding attenuation coefficient for a respective region of the scan region, including the volume of tissue and the acoustic coupling medium (such as the fluid of the tank in which the tissue is submerged). In particular, each acoustic attenuation slice can be created using a measure of attenuation of transmission signals and assuming a broad frequency band signal (or any suitable frequency band signal). Additionally or alternatively, each acoustic attenuation slice can be created on a frequency-dependent and/or transducer-dependent basis to account for frequency and directional dependence of absorption and scatter on the signal. Generating an acoustic attenuation map can additionally or alternatively include generating a 3D acoustic attenuation map that is a volumetric representation of the acoustic attenuation parameter within the volume of tissue, wherein generation of the 3D acoustic attenuation map can be implemented in a manner similar to the methods described above with regard to generating a 3D sound speed map. Additionally or alternatively, the acoustic attenuation map can be generated using methods as described in U.S. Pat. No. 8,663,113 and/or U.S. Pub. No. 2012/0283566, filed on 23 Jul. 2012, which are each incorporated herein in its entirety by this reference.

Block S150 recites: generating a stiffness map based upon a manipulation of the sound speed map and the acoustic attenuation map, which functions to transform the sound speed map and the acoustic attenuation map of Blocks S130 and S140, respectively, into a map that provides information regarding a distribution of stiffness across the region of the volume of tissue. Block S150 is preferably implemented at the processing system (e.g., computer processor) included with or coupled to the ultrasound tomographic scanner 200 of Blocks S110-S140, but can alternatively be implemented at any other suitable processing system. In Block S150, the stiffness map is preferably based upon a combination of elements of the sound speed map and elements of the acoustic attenuation map, and preferably, a combination of slices of a stack of 2D slices for sound speed, with corresponding slices of a stack of 2D slices for acoustic attenuation. As such, the stiffness map preferably describes a distribution of a stiffness parameter within a whole breast; however, the stiffness map can additionally or alternatively describe a distribution of the stiffness parameter within a region of a volume of breast tissue, wherein the region comprises a sub-portion of the whole breast. In variations, Block S150 can comprise generating a combined acoustomechanical parameter map derived from the sound speed map and the acoustic attenuation map S151, and transforming the combined acoustomechanical parameter map into the stiffness map S152.

In Blocks S151 and S152, a relationship between sound speed, acoustic attenuation, and stiffness (e.g., as represented by a bulk modulus) can be formed based upon a linking parameter (e.g., density), and the processing system (e.g., computer processor) can be configured to manipulate the sound speed map and the acoustic attenuation map according to the relationship, in order to generate the stiffness map and characterize regions of interest within the stiffness map. In one example of Blocks S151 and S152, acoustic wave propagation can be characterized by expression [1], wherein B represents a bulk modulus (i.e., a stiffness parameter representing a material's resistance to compression), c represents sound speed (e.g., longitudinal sound speed of a material), and $\rho$ represents density:

$$B \propto c^2 \rho \quad [1]$$

Given that sound speed (c) and density ($\rho$) are related by expression [2], where C1 and C2 are constants (and in a specific example, C1=1.12 and C2=0.391, with sound speed represented in mm/µs and density represented in g/cm$^3$):

$$c = C1 * \rho + C2 \quad [2]$$

Expressions [1] and [2] yield expression [3] as a relationship between sound speed and the bulk modulus:

$$B \propto c^3 \text{ or } c \propto B^{1/3} \quad [3]$$

Thus, sound speed has a dependence on the bulk modulus, which is a measure of stiffness.

In some variations, expression [3] above does not accurately represent some tissue masses (e.g., simple cysts), thus requiring a more complex model that incorporates an acoustic attenuation parameter, a. Given that acoustic attenuation (a) and density ($\rho$) are related by expression [4], where C3 and C4 are constants (and in a specific example, C3=3.38 and C4=−2.98, with acoustic attenuation represented in dB/cm at 1 MHz and density represented in g/cm$^3$), $$a = C3 * \rho + C4 \quad [4]$$

and constructing parameter $\Phi$ as the product of sound speed and acoustic attenuation and using expression (3), yields expression [5]:

$$\Phi = a * c \propto c^2 \propto B^{2/3} \quad [5]$$

Figure 4:
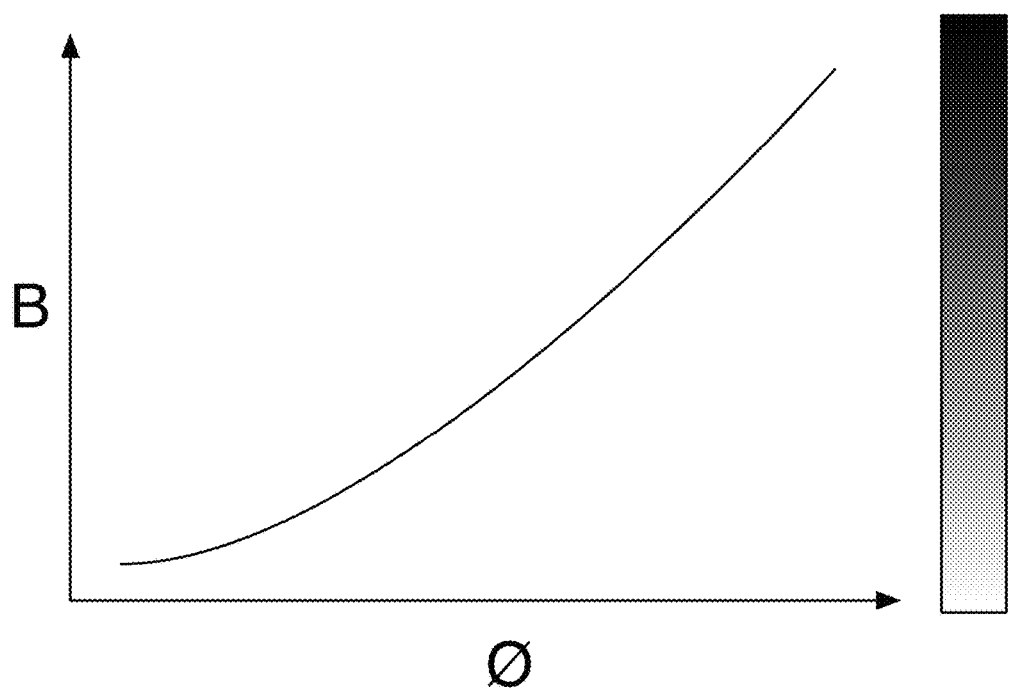
FIG. 4 depicts an exemplary relationship between sound speed, acoustic attenuation, and stiffness in an embodiment of a method representing tissue stiffness.

Thus, as shown in FIG. 4, $\Phi$ is functionally related to the bulk modulus, B, as a measure of stiffness, and produces a bulk modulus of zero when acoustic attenuation, a, is zero. Rearranging expression [5] gives expression [6], which describes stiffness in terms of parameter $\Phi$:

$$\Phi^{3/2} \propto B \quad [6]$$

In variations of the above expressions, however, any parameter or function of sound speed and/or acoustic attenuation, f(c,a), that has a suitable relationship with tissue stiffness (e.g., as represented by a bulk modulus parameter, B), can be substituted for $\Phi$. Furthermore, variations can additionally or alternatively implement additional acoustomechanical parameters (e.g., acoustic reflection, as shown in FIG. 3), in generating a relationship between a bulk modulus, B, and a set of acoustomechanical parameters.

Figure 5:
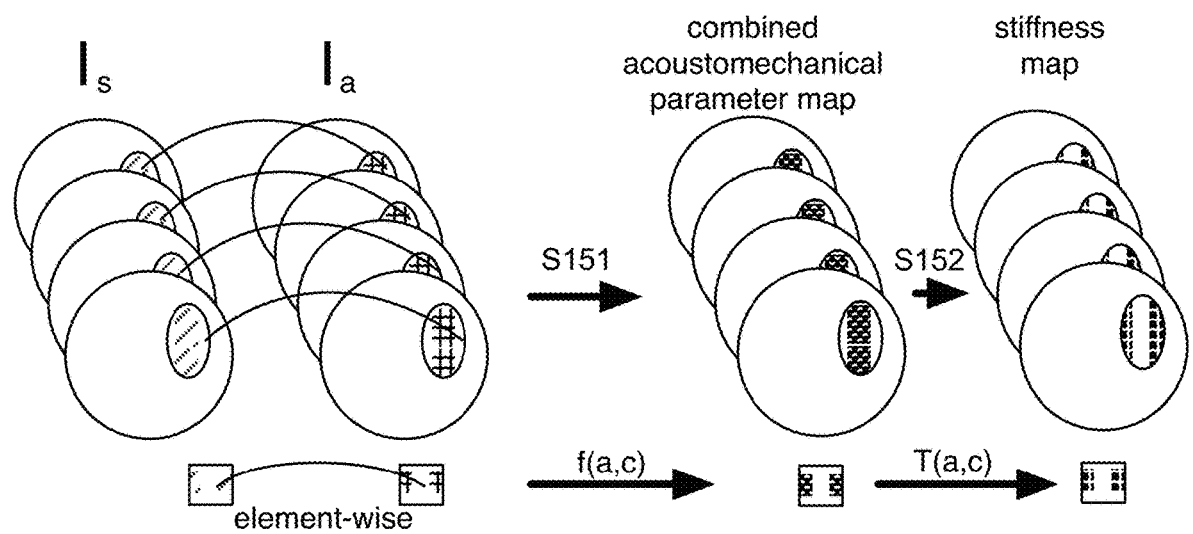
FIG. 5 depicts a variation of a portion of a method for representing tissue stiffness.

In one variation of Block S151, incorporating results of expressions [1] through [6] above, generating the stiffness map comprises combining a set of sound speed parameter values of the sound speed map and a corresponding set of acoustic attenuation parameter values of the acoustic attenuation map, the set of sound speed parameter values and the corresponding set of acoustic attenuation parameters associated with the set of elements of the region of the volume of tissue, and the stiffness map representing the distribution of the stiffness parameter across the region. In more detail, in one variation, Block S151 can comprise pairing each slice in the stack of 2D slices of sound speed with a corresponding slice in the stack of 2D slices of acoustic attenuation, as shown in FIG. 5, and multiplying (e.g., performing element-wise multiplication for) each sound speed slice with its paired acoustic attenuation slice to form the combined acoustomechanical parameter map comprising a stack of 2D slices. As such, the combined acoustomechanical parameter map of this variation of Block S151 includes a set of elements, each representing a product of sound speed and acoustic attenuation, such that the combined acoustomechanical parameter map represents a distribution of a product of sound speed and acoustic attenuation across a region of the volume of tissue. In this variation, Block S152 then comprises transforming the combined acoustomechanical parameter map into the stiffness map by taking each element of the combined acoustomechanical parameter map to a power of 3/2 to generate the stiffness map.

Alternative variations of Blocks S151 and S152 can alternatively comprise performing any other suitable operation on pairs of sound speed and acoustic attenuation slices for the volume of tissue, and transforming the combined slices as a combined acoustomechanical parameter map into a stiffness map in any other suitable manner. In some variations, for instance, combination of values of the sound speed map with corresponding values of the acoustic attenuation map can comprise weighting (e.g., weighting of sound speed values of the sound speed map, weighting of attenuation values of the attenuation map) element values prior to combination to form the combined acoustomechanical parameter map.

As suggested earlier with expressions [1] through [3] above, in some extreme variations of Block S150, the stiffness map can be based upon only one of the sound speed map and the acoustic attenuation map, such that the stiffness map is produced with lower computational effort, but also has lower accuracy in characterizing tissue stiffness for instance, in characterizing certain tissue masses (e.g., simple cysts). In one example of such a variation, generating the stiffness map can comprise taking each element of each slice in a stack of 2D slices for sound speed to an exponential power of 3 to generate a simplified stiffness map. Alternative variations of this specific example can, however, incorporate any other suitable model relating at least one acoustomechanical parameter and a measure of stiffness.

Furthermore, variations of Block S150 can additionally comprise conditioning a map (i.e., an sound speed map, an acoustic attenuation map, a combined acoustomechanical parameter map) to ensure that values of elements of the map do not have undesired values. As such, Block S150 can comprise Block S153, which recites: conditioning at least one of the sound speed map, the acoustic attenuation map, and the combined acoustomechanical parameter map in generation of the stiffness map. Block S153 functions to facilitate operations performed (e.g., mathematical operations performed on arrays) using the combined acoustomechanical parameter map and/or the stiffness map. As such, conditioning in Block S153 can comprise any one or more of increasing (e.g., uniformly increasing) intensity values of elements of a map, decreasing (e.g., uniformly decreasing) intensity values of elements of a map, scaling (e.g., uniformly scaling by a factor) intensity values of elements of a map, performing an absolute value operation on intensity values of elements of a map, and performing any other suitable manipulation on a map. In variations wherein the map(s) used to generate the stiffness map comprise a stack of 2D slices, the manipulation is preferably performed uniformly across each slice in the stack of slices, as well as uniformly across the stack of slices. However, the manipulation(s) can additionally or alternatively be performed in any suitable manner. In specific examples, conditioning can ensure that values of elements of a map (e.g., a sound speed map, an acoustic attenuation map, a combined acoustomechanical parameter map) do not have undesired values (e.g., negative values) that do not result in invalid mathematical operations when generating the stiffness map. In variations of the method 100 comprising Blocks S151, S152, and S153, Blocks S151-S153 can be performed in any suitable order.

Block S160 recites: rendering a stiffness image of the volume of tissue, based upon the stiffness map S160. The stiffness image is preferably rendered at a display of a user interface, wherein the display is in communication with the processing system (e.g., computer processor), such that the stiffness image can be provided to a user or an entity associated with the user having the volume of tissue analyzed. The stiffness image can, however, be rendered in any other suitable manner. The stiffness image preferably represents relative stiffness values between regions of the volume of tissue in a qualitative manner, but can additionally or alternatively be configured to represent quantitative values of stiffness since both c and a in expression (5) have quantitative values (e.g. km/s and dB/MHz/cm respectively) yielding quantities such as absolute stiffness and average stiffness within the volume of tissue. In variations, stiffness can be represented by the stiffness image with one or more visual cues, based upon the stiffness map of Block S150, including any one or more of: a distribution of colors corresponding to different stiffness values or ranges of stiffness values, a distribution of patterns corresponding to different stiffness values or ranges of stiffness values, a distribution of shading (e.g., intensity) corresponding to different stiffness values or ranges of stiffness values, a distribution of a saturation parameter corresponding to different stiffness values or ranges of stiffness values and any other suitable method of representing a distribution of a parameter within a volume of tissue.

In some variations of Block S160, rendering the stiffness image can include defining one or more regions within the volume of tissue, generating an average stiffness value for each region based upon the stiffness map, and generating the stiffness image using a visual cue (e.g., color, pattern, shading) having a discrete distribution corresponding to the average stiffness values for the regions to provide information regarding local stiffness. In an alternative variation, rendering the stiffness image may not include defining one or more regions within the volume of tissue, but instead use a visual cue (e.g., color, pattern, shading) having a continuous distribution corresponding to a continuous range of stiffness values to provide a visual representation of stiffness across a continuum of the volume of tissue.

The stiffness image of Block S160 can be rendered in isolation, but can additionally or alternatively be overlaid with any one or more of: an image generated from the sound speed map, an image generated from the acoustic attenuation map, an image generated from an acoustic reflection map, any image generated from a merging of maps representing different acoustomechanical parameters (e.g., sound speed, acoustic attenuation, acoustic reflection), and any other suitable image of the volume of tissue. In one variation, the stiffness image can be overlaid with an enhanced image of the volume of tissue, for instance, an enhanced B-mode image processed with a transfer map (e.g., generated from one or more of an sound speed map and an acoustic attenuation map) configured to provide an enhanced B-mode image of the volume of tissue.

Figure 6A:
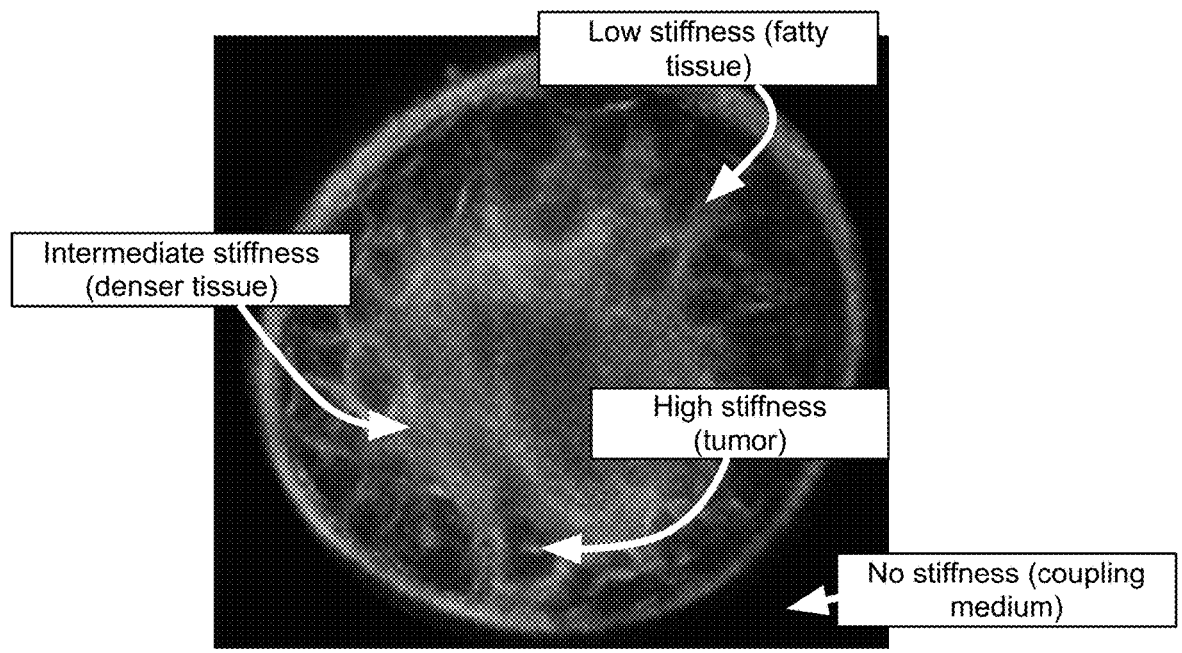
FIGS. 6A and 6B depict example output images of a method for representing tissue stiffness.
Figure 6B:
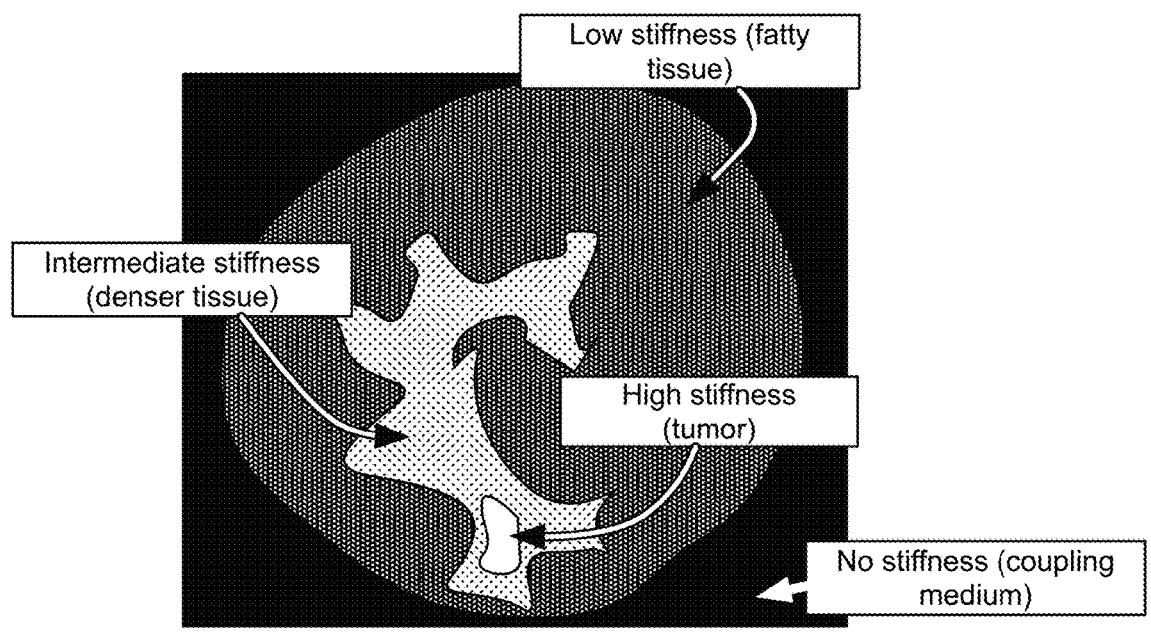

In a specific example of Block S160, as shown in FIG. 6A, a stiffness image with a distribution of colors representing different stiffness values is overlaid with an B-mode image of a volume of breast tissue, wherein a first color represents high stiffness within the volume of breast tissue (e.g., corresponding to a tumorous mass), a second color represents intermediate stiffness within the volume of breast tissue, a third color represents low stiffness within the volume of breast tissue (e.g., corresponding to a fatty mass), and a fourth color represents no stiffness within the volume of breast tissue (e.g., corresponding to an acoustic coupling medium surrounding the volume of breast tissue during scanning). In another specific example of Block S160, as shown in FIG. 6B, a stiffness image with a distribution of patterns representing different stiffness values is generated, wherein a first pattern of dots having high density represents high stiffness within the volume of breast tissue (e.g., corresponding to a tumorous mass), a second pattern of dots having intermediate density represents intermediate stiffness within the volume of breast tissue, a third pattern of dots having low density represents low stiffness within the volume of breast tissue (e.g., corresponding to a fatty mass), and a fourth pattern without dots represents no stiffness within the volume of breast tissue (e.g., corresponding to an acoustic coupling medium surrounding the volume of breast tissue during scanning). Variations of the examples of the stiffness image can, however, be constructed in any other suitable manner.

In some variations, the method 100 can further include Block S170, which recites: providing an indication of at least one tissue mass within the volume of tissue, based upon the stiffness image, at a user interface. Block S170 functions to provide information regarding presence of a distribution of different tissue types within the volume of tissue, and can be used to indicate presence of a cancerous mass, or risk of developing a cancerous mass within the volume of tissue, as assessed using at least one of the stiffness image and the stiffness map. Block S170 is preferably implemented at the processing system (e.g., computer processor) included with or coupled to the ultrasound tomographic scanner 200 of Blocks S110 and S120, but can alternatively be implemented at any other suitable processing system. As such, Block S170 can comprise generating an analysis at a module of the processing system, wherein generating the analysis includes generating the indication of presence of at least one target mass within the volume of tissue. In some embodiments of Block S170, the indication can characterize a distribution of different tissue types within the volume of tissue, as represented by indicative values or ranges of values of the stiffness parameter (e.g., bulk modulus, B) across the volume of tissue. As such, the stiffness map/stiffness image (e.g., a 3D map or image, a 2D map or image, etc.) can characterize a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), cyst tissue, and any other suitable tissue type within the volume of tissue. In generating the indication, a first stiffness range (e.g., high stiffness values across a region of interest) can be associated with cancerous tissues, a second stiffness range (e.g., mixed stiffness values across a region of interest, medium stiffness values across a region of interest) can be associated with fibroadenoma tissues, and a third stiffness range (e.g., low stiffness values across a region of interest) can be associated with cyst tissues.

In Block S170, the indication can be provided visually, for instance, using outlines or arrows to direct a viewer toward regions of the volume of tissue having the tissue mass(es) of interest. The indication can additionally or alternatively be provided in a text and/or audio format, by describing the location(s) of the tissue mass(es) within the volume of tissue, using anatomical terms of location. In some variations, the indication can further indicate quantitative values of the stiffness parameter(s) for the tissue mass(es), and/or an assessment of risk that the tissue mass(es) are pathological or will develop into pathological masses in the future. Variations of the indication, can, however, be provided in any other suitable manner.

In relation to provision of the indication in Block S170, the indication is preferably provided to an entity analyzing the volume of tissue, wherein the entity can comprise a human entity or a computing entity (e.g., processing system, remote server, computer processor, cloud computing system, etc.). In variations, the human entity can include one or more of: a healthcare provider, a radiologist, a technician, a physician, a nurse, a caretaker, a system operator, a relative, an acquaintance, and any other suitable entity associated with the patient and/or interested in analysis of the volume of tissue.

The method 100 can, however, include any other suitable blocks or steps that facilitate detection, processing, and/or analyzing of acoustic signals generated from a volume of tissue of the user in a manner that provides a representation of stiffness within the volume of tissue. For instance stiffness modeling for the volume of tissue, over a set of time points (e.g., related to disease progression, related to treatment) can be used to monitor states of identified masses within the volume of tissue over time. Identification of changes in stiffness, in temporally spaced analyses of the volume of tissue, can be used to track changes in mass size and/or mass state (e.g., a transition from a non-spreading state to a spreading state, a transition to a state of remission, etc.) for a patient. Furthermore, as a person skilled in the art will recognize from the previous detailed description and from the figures and claims, modifications and changes can be made to the preferred embodiments of the method 100 without departing from the scope of method 100.

2. System

As shown in FIGS. 2A-2C, a system 200 for determining a distribution of a stiffness parameter within a volume of tissue comprises: a transducer 220 configured to receive the volume of tissue and comprising an array of ultrasound transmitters 110 and an array of ultrasound receivers 120, the array of ultrasound transmitters 110 configured to emit acoustic waveforms toward the volume of tissue and the array of ultrasound receivers 120 configured to detect a set of acoustic signals derived from acoustic waveforms transmitted through the volume of tissue; a computer processor 210 in communication with the transducer, the computer processor 210 comprising: a first module 212 configured to output a sound speed map of a region of the volume of tissue, the region including a set of elements; a second module 214 configured to output an acoustic attenuation map of the region of the volume of tissue; a third module 216 configured to receive outputs of the first module and the second module and to output a stiffness map derived from element-wise multiplication of the sound speed map and the acoustic attenuation map, the stiffness map representing the distribution of the stiffness parameter across the region; and a display 290 in communication with the computer processor 210 and configured to render a stiffness image of the volume of tissue, based upon the stiffness map, including an indication of presence of a target mass within the volume of tissue.

The system 200 functions to render ultrasound images and/or generate transformed ultrasound data that can be used to provide an indication of a distribution of tissue stiffness within a volume of tissue. In some embodiments, the system 200 can function to produce images that are aligned with regulatory standards for medical imaging, as regulated, for instance, by the U.S. Food and Drug Administration (FDA). The system 200 is preferably used to characterize stiffness within tissue of a human breast, and more specifically, to characterize stiffness across a volume of a whole breast of a human patient. However, the system 200 can additionally or alternatively be used to characterize stiffness within tissue of an arm, leg, other appendage, and/or any suitable volume of tissue in a human or other animal. In relation to pathogenic masses, the system 200 can provide significant improvements over currently available methods and systems (e.g., mammographic methods and systems), in particular, for dense tissues. Even further, the method 100 can enable detection of node-negative invasive cancers that typically progress to a more severe stage prior to mammographic detection. In relation to current ultrasound methods and systems, the system can improve sensitivity in detection of suspicious masses, while providing specificity in characterization of types of masses (e.g., in comparison to reflection ultrasound alone). The system 200 can, however, function to enable diagnosis, monitoring, and/or characterization of a volume of tissue in any other suitable manner. The system 200 is preferably configured to implement at least a portion of an embodiment, variation, or example of the method 100 described in Section 1 above; however, the system 200 can additionally or alternatively be configured to implement any other suitable method.

The transducer 220, the computer processor 210, and the display 290 are preferably coupled to a scanner table 205, as shown in FIGS. 2A and 2B, wherein the scanner table 205 has an opening 206 that provides access to the volume of tissue 10 of the patient. The table, which may be made of a durable, flexible material (e.g., flexible membrane, fabric, etc.), preferably contours to the patient's body, thereby increasing scanning access to the axilla regions of the breast and increasing patient comfort. The opening 206 in the table allows the breast (or other appendage) to protrude through the table and be submerged in an imaging tank 230 filled with water or another suitable fluid as an acoustic coupling medium that propagates acoustic waves.

As shown in FIGS. 2B and 2C, a ring-shaped transducer 220 with transducer elements 222 can be located within the imaging tank 230 and encircle or otherwise surround the breast, wherein each of the transducer elements 222 can comprise one of the array of ultrasound transmitters 110 paired with one of the an array of ultrasound receivers 120. Multiple ultrasound transmitters 110 that direct safe, non-ionizing ultrasound pulses toward the tissue, and multiple ultrasound receivers 120 that receive and record acoustic signals scattering from the tissue and/or transmitted through the tissue, are distributed around the ring transducer 220. In one configuration, the transducer 220 can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 2C. During the scan, the ring transducer 220 passes along the tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The transducer 220 can be configured to scan step-wise in increments from the chest wall towards the nipple, and/or from the nipple towards the chest wall. However, the transducer 220 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014, which is hereby incorporated in its entirety by this reference. Furthermore, in a specific example, the system 200 can implement a ring transducer 220 having 2048 transducer elements in cooperation with an ultrasound tomographic scanner 200 having 512 receive channels, 512 transmit channels, an operating frequency of 3 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. However, system 200 can additionally or alternatively comprise or be coupled with any other suitable patient interface system.

The computer processor 210 can be implemented in one or more computing systems, wherein the computing system(s) can be implemented at least in part in the cloud and/or as a machine (e.g., computing machine, server, etc.) configured to receive a computer-readable medium storing computer-readable instructions. Additionally or alternatively, the computer processor can be implemented on one or more computer networks, computer systems, or applications servers, etc., wherein the computer system(s) can comprise one or more of: a cloud-based computer, a mainframe computer system, a grid-computer system, or any other suitable computer system. In one variation, the first module 212, the second module 214, and the third module 216 of the computer processor 210 are implemented as software modules executing on a computer machine coupled to the scanner table 205 and in communication with the display 290; however, the computer processor 210 can additionally or alternatively be implemented using any other suitable computing system architecture.

The system 200 can include any other suitable elements that facilitate detection, processing, and/or analyzing of acoustic signals generated from a volume of tissue of the user in a manner that provides a representation of stiffness within the volume of tissue. Furthermore, as a person skilled in the art will recognize from the previous detailed description and from the figures and claims, modifications and changes can be made to the preferred embodiments of the system 200 without departing from the scope of system 200.

3. Method and System—Specific Application

In a specific application of the method 100 and system 200, a stiffness image, generated from combination of a sound speed map and an acoustic attenuation map, was overlaid on a grayscale B-mode ultrasound image, wherein the stiffness image depicted fibroadenoma tissue and cancer tissue as being stiffer than surrounding "normal" tissue, while simple cyst tissue was depicted as being softer than surrounding normal tissue.

In the specific application, as applied to a breast phantom having 7 masses of differing size, types (e.g., cancer tissue, fibroadenoma tissue, cyst tissue), and positions, as shown in FIG. 7A, the method and system were able to accurately estimate stiffness values (i.e., in comparison to stiffness values provided by a manufacturer of the breast phantom) based upon combination of sound speed and acoustic attenuation parameters for the volume of tissue. In the specific application, as applied to 13 patients in an in vivo study (represented in FIG. 7B), the method and system were able to accurately estimate stiffness values for cancerous masses with 100% accuracy, fibroadenoma masses with high accuracy, and cyst masses with high accuracy, based upon combination of sound speed and acoustic attenuation parameters for the volume of tissue. Finally, in an elastography-based validation, the specific application of the method 100 and system 200 characterized stiffness for 11 volumes of tissue—each associated with different breast sizes (e.g., A cup to G cup), and each having varying densities (e.g., fatty, scattered, heterogeneous, dense, extremely dense), each having various types of lesions (e.g., cysts, fibroadenomas, cancers), each having various sizes of lesions (e.g., 8 mm-43 mm)—as well as a system implementing a gold-standard elastography measurement module (shown in FIG. 7C). Thus, the specific application of the method 100 and system 200, using ultrasound alone, were demonstrated to provide stiffness distribution characteristics of a volume of tissue in a manner that could substitute for or supplement elastography-based measurements (e.g., measurements involving tissue distortion to assess stiffness).

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be implemented in the cloud, and/or stored on any suitable computer-readable media such as RAMs, ROMs, flash memory, EEPROMs, optical devices (CD or DVD), hard drives, solid state drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

What is claimed is:

1. A system for determining a distribution of a stiffness parameter within a volume of tissue, the system comprising:
    a transducer configured to receive the volume of tissue and comprising an array of ultrasound transmitters and an array of ultrasound receivers, the array of ultrasound transmitters configured to emit acoustic waveforms toward the volume of tissue and the array of ultrasound receivers configured to detect a set of acoustic signals derived from acoustic waveforms transmitted through the volume of tissue;
    a processor in communication with the transducer, the processor comprising instructions which when executed are configured to:
        output a sound speed map of a region of the volume of tissue, the region including a set of elements;
        output an acoustic attenuation map of the region of the volume of tissue;
        output a stiffness map derived from element-wise multiplication of the sound speed map and the acoustic attenuation map, the stiffness map representing the distribution of the stiffness parameter across the region of the volume of tissue; and
        based upon the stiffness map, render a stiffness image of the volume of tissue, wherein the stiffness image includes an indication of presence of a target mass within the volume of tissue, at a display in communication with the processor.

2. The system of claim 1, wherein the transducer comprises a ring transducer, wherein an opening of the ring transducer is configured to receive the volume of tissue.

3. The system of claim 2, wherein the array of ultrasound transmitters and the array of ultrasound receivers are arranged about the ring transducer in an axially symmetric manner about the opening of the ring transducer.

4. The system of claim 1, wherein the processor further comprises instructions which when executed are configured to apply an exponential function to each element of the element-wise multiplication of the sound speed map and the acoustic attenuation map to generate the stiffness map.

5. The system of claim 1, wherein the transducer is configured to pass along the volume of tissue, submerged in an imaging tank with a coupling medium, in an anterior-posterior.

6. The system of claim 1, wherein the processor does not comprise instructions configured to generate an elastography measurement for the volume of tissue.

7. The system of claim 1, wherein the processor comprises instructions which are configured to generate an analysis that describes the target mass as a) a cancerous mass if the target mass is associated with high stiffness values, b) a fibroadenoma if the target mass is associated with a combination of high and low stiffness values, and c) a cyst if the target mass is associated with low stiffness values.

8. The system of claim 1, wherein the processor comprises instructions which are configured to generate at least one of the acoustic attenuation map, the sound speed map, and the stiffness map from a set of coronal slices through the volume of tissue.

9. The system of claim 7, wherein the processor comprises instructions which are configured to monitor changes in stiffness across the volume of tissue based on the analysis that describes the target mass.

10. The system of claim 1, wherein the processor comprises instructions which are configured to generate an analysis that determines a severity or a stage of the target mass.

11. The system of claim 1, wherein the processor comprises instructions which are configured to generate an analysis that determines whether the target mass is surgically removable.

12. The system of claim 1, wherein the transducer is configured to emit acoustic waveforms at a frequency within a range of 1-20 Mhz.

13. The system of claim 1, wherein the element-wise multiplication of the sound speed map and the acoustic attenuation map further comprises a weighting of either the sound speed map or the acoustic attenuation map.

14. The system of claim 1, wherein the processor comprises instructions configured to condition the sound speed map, the acoustic attenuation map, or the stiffness map by one or more of uniformly scaling by a factor, uniformly decreasing, and performing an absolute value operation.

15. The system of claim 1, wherein the stiffness image of the volume of tissue comprises one or more of: a distribution of colors, a distribution of patterns, a distribution of shading, and a distribution of a saturation parameter.

16. The system of claim 1, wherein the processor comprises instructions to generate an average stiffness value for the region of the volume of tissue.

17. The system of claim 1, wherein the stiffness image comprises an overlay of one or more of: the sound speed map, the acoustic attenuation map, and the acoustic stiffness map.

18. The system of claim 1, wherein the processor and the display are coupled to a scanner table, wherein the scanner table comprises an opening that provides access to the volume of tissue.

19. The system of claim 18, wherein the opening provides access to the volume of tissue when a patient is prone.

20. The system of claim 1, wherein the volume of tissue is a patient breast.

* * * * *

UNITED STATES PATENT AND TRADEMARK OFFICE
CERTIFICATE OF CORRECTION

| | |
|---|---|
| PATENT NO. | : 11,147,537 B2 |
| APPLICATION NO. | : 16/182715 |
| DATED | : October 19, 2021 |
| INVENTOR(S) | : Nebojsa Duric et al. |

It is certified that error appears in the above-identified patent and that said Letters Patent is hereby corrected as shown below:

In the Specification

In Column 1, Line 12, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Thirtieth Day of July, 2024

Katherine Kelly Vidal
*Director of the United States Patent and Trademark Office*